(12) United States Patent  
Schmidt et al.

(10) Patent No.: US 7,189,975 B2  
(45) Date of Patent: Mar. 13, 2007

(54) WIRE-FREE, DUAL-MODE CALIBRATION INSTRUMENT FOR HIGH ENERGY THERAPEUTIC RADIATION

(75) Inventors: Daniel G. Schmidt, Blanchardville, WI (US); Myles L. Sommerfeldt, Madison, WI (US); Kevin L. DeFever, Waunakee, WI (US); Thomas C. Bonde, Blue Mounds, WI (US)

(73) Assignee: Standard Imaging, Inc., Middleton, WI (US)

( * ) Notice: Subject to any disclaimer, the term of this patent is extended or adjusted under 35 U.S.C. 154(b) by 338 days.

(21) Appl. No.: 10/774,817

(22) Filed: Feb. 9, 2004

(65) Prior Publication Data

US 2005/0173648 A1    Aug. 11, 2005

(51) Int. Cl.  
*H01J 47/02* (2006.01)

(52) U.S. Cl. .................... 250/374; 250/385.1; 378/207
(58) Field of Classification Search ................ 250/374, 250/200, 207, 252.1, 370.01, 370.05, 370.06, 250/370.07, 385.1, 305, 389; 378/207  
See application file for complete search history.

(56) References Cited

U.S. PATENT DOCUMENTS

| | | | | |
|---|---|---|---|---|
| 3,942,012 A | | 3/1976 | Boux | |
| 4,124,527 A | * | 11/1978 | Kauffman | .................... 436/536 |
| 4,206,355 A | | 6/1980 | Boux | |
| 4,300,050 A | | 11/1981 | Hizo et al. | |
| 4,516,028 A | * | 5/1985 | Riggan | .................. 250/370.06 |
| 4,558,223 A | * | 12/1985 | Broadhurst et al. | ......... 250/374 |
| 4,568,828 A | | 2/1986 | Collica | |
| 4,988,866 A | | 1/1991 | Westerlund | |
| 5,120,967 A | * | 6/1992 | Cappelli et al. | ......... 250/385.1 |
| 5,336,889 A | | 8/1994 | Hofstetter | ............... 250/361 R |
| 5,410,155 A | * | 4/1995 | Thomson et al. | ........... 250/364 |
| 5,621,214 A | | 4/1997 | Sofield | |
| 5,680,423 A | * | 10/1997 | Perkins et al. | .............. 376/153 |
| 6,225,622 B1 | | 5/2001 | Navarro | |
| 6,542,565 B2 | * | 4/2003 | Ruddy et al. | ................ 376/153 |
| 6,885,007 B2 | * | 4/2005 | Donaghue et al. | .......... 250/394 |
| 7,064,338 B2 | * | 6/2006 | El-Hanany et al. | ......... 250/374 |
| 2004/0178388 A1 | * | 9/2004 | Mumper et al. | ....... 252/301.17 |

* cited by examiner

*Primary Examiner*—David Porta  
*Assistant Examiner*—Faye Boosalis  
(74) *Attorney, Agent, or Firm*—Boyle Fredrickson Newholm Stein & Gratz S.C.

(57) ABSTRACT

An instrument for checking quality of therapeutic x-ray and electron radiation provides modes optimized for both electrons and for photons obtained by physically flipping the unit to interpose the necessary build-up material between the radiation beam and contained detectors. The invention provides an improved method of constructing ionization detectors for improved energy discrimination using such detectors and wire-free operation.

18 Claims, 4 Drawing Sheets

WIRE-FREE, DUAL-MODE CALIBRATION INSTRUMENT FOR HIGH ENERGY THERAPEUTIC RADIATION

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention relates to quality assurance instruments for medical radiotherapy equipment used for radiation treatment of tumors or the like.

Cancerous tumors may be treated by irradiating the tumor with high-energy photons or electrons (henceforth both termed "radiation").

Such radiotherapy relies in part on the fact that tumor tissue is more sensitive than normal tissue to such high-energy radiation. Nevertheless, the radiation dose must be carefully controlled to limit the exposure of healthy tissue while ensuring sufficient radiation is received by the tumor.

Radiation dose may be controlled by a variety of means including shutters for collimating the radiation beam to the area of the tumor, filters for varying the intensity of radiation within the area of the tumor, and control of the exposure duration. An accurate understanding of the energy, flux, and alignment of the radiation beam is essential for such control. Generally, as is understood in the art, radiation energy describes the average energy of the individual photons or electrons whereas radiation flux is number of electrons or photons per unit area per unit time.

Radiation energy may be determined by calculating changes in flux at two depths within a homogenous medium, for example, a water phantom.

Radiation flux is normally determined using an ionization chamber or semiconductor detector placed in the radiation beam at a fixed distance from the radiation source. A "build-up" material such as a plastic block may be placed in front of the flux-detector to improve its sensitivity. For the purposes of periodic quality assurance of a radiotherapy machine, the output of the flux-detector may be compared to a base line for the same detector. In this way, precise calibration of the detector to a standard is not required.

Radiation alignment is normally determined with respect to a visible light field projected along with the radiation showing, for example, an illuminated rectangular area and/or cross-hair pattern. Alignment may be verified by exposing a film marked to show the location of the light field or crosshairs and comparing the exposed film to the markings. Alternatively, as shown in U.S. Pat. No. 4,988,866, a fixture having multiple ionization detectors and multiple light detectors (also called edge detectors) may be used, and the signals from the ionization detectors and light detectors may be compared.

It is desirable that the radiation therapy machine be checked on a frequent, periodic basis at each of its settings. Such quality assurance checks can be cumbersome and time consuming particularly when multiple pieces of test equipment must be used, for example, as would be required to calibrate a radiotherapy machine that provides both electron beams and photon beams at a variety of energy levels. It is difficult to construct a quality assurance instrument that works for a wide variety of different radiation energies and different radiation modes, e.g. electrons or photons, equally well.

BRIEF SUMMARY OF THE INVENTION

The present invention provides a radiation beam checker that may verify flux profiles and constancy for a wide variety of radiation energies and modes. Several features contribute to this versatility. First, the beam checker may receive radiation from either of two directions, flipping to receive electrons through one side and photons through the other. In this way, a single set of detectors may be optimized for either of two different radiation modes. Second, rather than relying on a single filtered and unfiltered detector to determine energy level, the present invention may use multiple detectors, each having a different filtration to provide data for a more sophisticated energy discrimination function accurate over a wide energy range. Visual fiducia on both surfaces of the beam checker allow alignment to be determined by flux measurements from the multiple flux-detectors without the need for photosensitive edge detectors that would be required on both surfaces.

One embodiment of the present invention permits wire-free operation simplifying manipulation of the beam checker without requiring radio communication that may be difficult to establish in the environment of the radiotherapy machine. An additional feature of one embodiment of the present invention is automatic linkage of data to energy levels to minimize necessary operator input. In one embodiment, the present invention may employ a new construction technique for ionization detectors simplifying the manufacture and improving the consistency of multi-detector systems.

Specifically then, the present invention may provide a test apparatus for both photon and electron radiation, the test apparatus having a housing providing opposed first and second faces holding a set of detectors between the first and second faces. In this embodiment, a first calibrating material for electrons is positioned to intercept electrons passing through the first face to the detectors, and a second calibrating material for photons is positioned to intercept photons passing through the second face to the detectors.

It is thus one object of the invention to provide a single test unit that may be tailored to two modes of radiation by placing different build-up or filter materials on the opposite faces of the housing and flipping the housing according to the radiation mode.

The test apparatus may include a quantitative radiation measurement display on a third face of the housing visible when either the second or first face is lying on the surface. The display may change orientation according to whether electrons or photons are being measured to be upright to an operator in either mode.

Thus, it is another object of the invention to provide a device that retains ease of use in either orientation of the housing.

One embodiment the invention provides a wire-free test apparatus for therapeutic radiation systems having a housing holding a set of radiation detectors for measuring radiation flux at predetermined locations and a solid state memory for receiving and storing the radiation flux measurements. A battery within the housing powers the radiation detectors and solid-state memories and a port is provided on the housing for downloading the stored radiation flux measurements to a remote computer.

Thus, it is another object of the invention to provide an easily maneuverable test device unencumbered by connecting cables. It is another object of the invention to provide wire-free operation without the need for radio transmission of data such as can be blocked by the shielding used around radiotherapy machines.

The housing may include a light field guide on its surface, delineating a region of the housing containing the detectors that should be exposed to radiation. The processing circuitry and memory may be within the housing outside of the region.

Thus, it is another object of the invention to provide a simple method of minimizing radiation exposure to solid-state memory which is normally sensitive to radiation damage or interference.

The processing circuitry contained within the housing may communicate with at least some of the radiation detectors to detect the start of a new radiation measurement from signals produced by the radiation detectors and to automatically store the radiation measurements in the solid state memory.

Thus, it is another object of the invention to provide for simplified data acquisition without the need for complex keyboard control or a permanently attached remote terminal.

In one embodiment, the invention provides a beam checker for therapeutic radiation comprising a set of spaced radiation flux-detectors producing flux signals and at least one radiation energy-detector providing an energy signal and a storage system for storing a set of energy ranges. Processing circuitry compares at least one of the flux signals to benchmark flux values of an energy range corresponding to the energy signal to provide an indication of any improper operation of the measured radiation source. Generally, the benchmark flux values may indicate flatness, symmetry, or constancy over time.

Thus, it is an object of the invention to use the energy signal to automatically relate flux measurements to proper benchmark measurements for different energy ranges.

The radiation energy-detector may be a set of at least three detector elements having different filtrations to provide radiation signals and the energy signal may be derived from an algebraic combination of the radiation signals from the set of detector elements. Alternatively or in addition, the radiation detector may be a set of detector elements, at least one of which element has a "backscatter element" positioned behind it with respect to the measured radiation so that the detector element is sensitive to backscatter, and the energy signal may be derived from an algebraic combination of the radiation signals.

Thus it is one object of the invention to provide an improved low-profile energy sensor that works over a wider range of energy values than can be achieved with a single filtered detector.

One embodiment of the invention provides an ionization detector that includes a front and rear plate positioned on a front and rear side of a volume of ionizable gas or other fluid to receive a voltage thereacross to collect the charges resulting from radiation ionizing the gas. The rear plate may be formed of a printed circuit board providing a collector on its front surface and multiple layers, including a middle layer providing a signal trace and a first and second ground flanking the middle layer, where the signal trace may connect to the collector.

Thus it is an object of the invention to provide improved manufacturability for ionization detectors by using the fabrication techniques associated with printed circuit boards while providing the shielding needed to protect the faint ionization signals.

These particular objects and advantages may apply to only some embodiments falling within the claims and thus do not define the scope of the invention.

DETAILED DESCRIPTION OF THE PREFERRED EMBODIMENT

Figure 1:
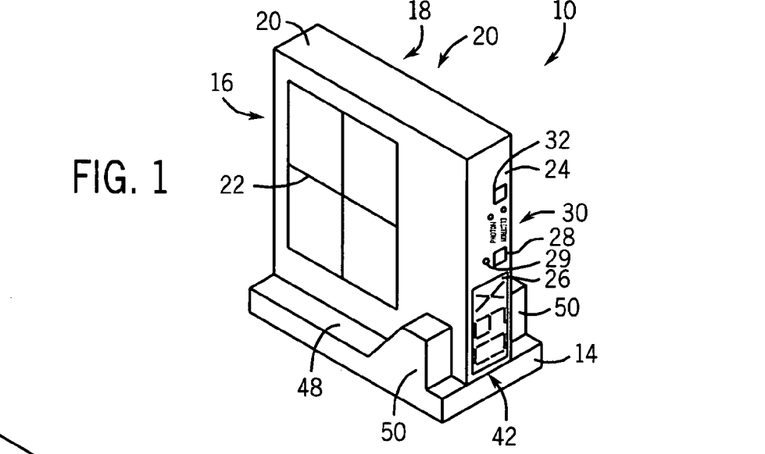
FIG. 1 is a perspective view of the beam checker of the present invention as held in a cradle prior to use showing a first side for receiving photon radiation.

Referring now to FIG. 1, the beam checker 10 of the present invention provides a mobile detecting unit 12 having a generally rectangular, box-shaped housing 20 providing a first photon-receiving face 16 opposed to a second electron-receiving face 18.

Referring also FIG. 2, a portion of the photon-receiving face 16 and electron-receiving face 18 is marked with a target 22 defining an area of radiation exposure and thus providing a means for aligning the housing 20 of the mobile detecting unit 12 with a light field or laser crosshair provided by standard radiotherapy machines, as will be described. Typically, the target 22 or 22' is 20 cm by 20 cm and includes a crosshair dividing the target area into equal quadrants.

Figure 2:
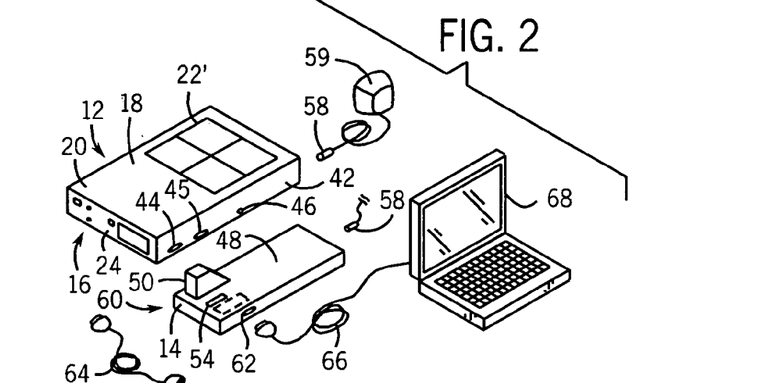
FIG. 2 is a perspective view of the beam checker and cradle (in partial phantom) together with various cables, a remote computer, and charging unit as may be used with the beam checker; and showing a second side for receiving electron radiation.
Figure 3:
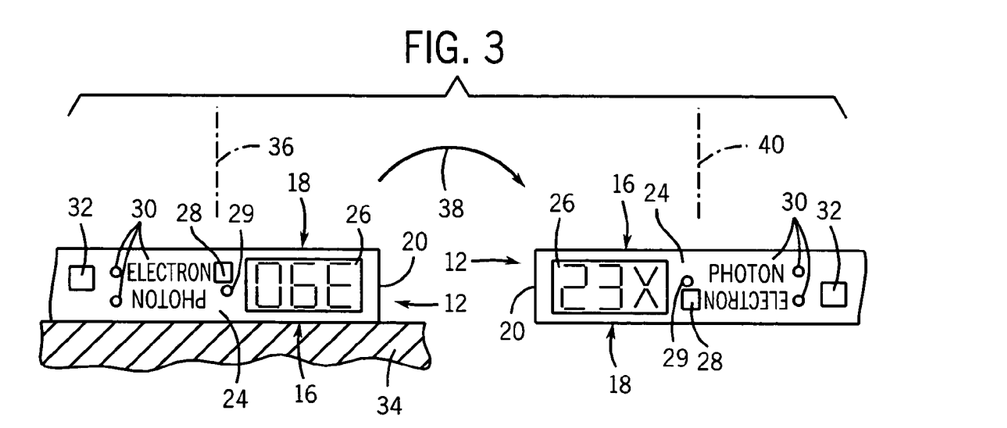
FIG. 3 is a front elevational view of a third wall of the beam checker of FIGS. 1 and 2 as supports a display of radiation energy such as may flip in orientation, depending on the particular radiation mode being detected.

Referring to FIGS. 2 and 3, a first side wall 24 of the housing 20 holds a three-character, 1.2 inch tall, seventeen-segment light emitting diode (LED) alphanumeric display 26, a reset button 28 and a separate bicolor LED 29, radiation mode captions and lamps 30, and a mode select button 32. During operation, side wall 24 remains visible when either of the photon-receiving face 16 or electron-receiving face 18 of the housing 20 are supported by structure of the radiation therapy machine, for example, a horizontal patient support 34.

When photon-receiving face 16 is against the patient support 34, electron-receiving face 18 is upward facing a source of radiation along axis 36. The operator may then press the mode select button 32 to illuminate a lamp next to the radiation mode caption denoting "electron" and to indicate to the beam checker 10 that this is the type of radiation being measured. The caption "electron" will be right side up when the housing 20 is appropriately oriented for receiving electron radiation.

Upon exposure of the beam checker 10 to electron radiation, the alphanumeric display 26 will display a detected energy range using both alphabetic and numeric characters. Typically, the energy ranges will include 6E, 9E, 12E, 16E, and 22E. The number being a measure of energy in MeV and the "E" suffix indicates that the beam checker 10 is checking for electron radiation. The alphanumeric display will be automatically oriented to be right side up, based on the mode selected, when the beam checker is correctly positioned to receive electron radiation as described. This reorientation requires simply a change in the mapping of segments of the alphanumeric display 26 and can be accomplished electronically by the contained processor described below.

The housing 20 may be flipped as shown by arrow 38 so that photon-receiving face 16 is upward to receive a beam of photons along axis 40. The operator may then press the mode select button 32, but this time to illuminate a lamp next to the radiation mode caption denoting "photon" and to indicate to the beam checker 10 that this is the type of radiation being measured. The caption "photon" is inverted with respect to the caption "electron" to be right side up when the housing 20 is appropriately oriented for receiving photon radiation.

Upon exposure of the beam checker 10 to photon radiation, the alphanumeric display 26 will display a detected energy range using both alphabetic and numbers typically 6X, 18X or 23X with the number being a measure of energy in MV and the "X" suffix indicates that the beam checker 10 is checking for x-ray photons. As before, the alphanumeric captions will be automatically oriented to be right side up based on the mode selected. Thus it will be understood that the alphanumeric display 26, reset button 28, LED 29, radiation mode captions and lamps 30, and a mode select button 32 may be readily used with either orientation of the housing 20.

Referring again to FIGS. 1 and 2, a second side wall 42 of housing 20 of the beam checker 10, spanning electron-receiving face 18 and photon-receiving face 16, provides on its surface a data/power connector 44, a data-only connector 45, and power connector 46. When the mobile detecting unit 12 is placed within the cradle 14, the side wall 42 abuts an upper face 48 of the cradle 14 so that data/power connector 44 connects with a corresponding data/power connector 52 and power connector 54 on the upper face 48 of the cradle 14. In this way, data may be communicated to and from the mobile detecting unit 12 and power may be provided to the mobile detecting unit 12.

The mobile detecting unit 12 is held in position on the cradle 14 by two guiding pylons 50 extending upward from the cradle 14 and abutting the electron-receiving face 18 and photon-receiving face 16. Note that in FIG. 2 one guiding pylon 50 is removed for clarity.

The cradle 14 includes provisions to receive a power cord 58 which may provide line power from a standard wall transformer 59, or the like, to the mobile detecting unit 12 through power connector 54. Alternatively, the power cord 58 may be received directly by the mobile detecting unit 12 at power connector 46.

Cradle 14 also incorporates two RS-232 connectors 60 and 62 which electrically communicate with data/power connector 52 (connector 60 is opposite connector 62 and not visible in FIG. 2). Connectors 60 and 62 allow the mobile detecting unit 12 to be connected to the cradle 14 by means of a standard RS-232 cable 64 connecting between RS-232 connector 60 and data/power connector 44 on the mobile detecting unit 12 when mobile detecting unit 12 is not sitting on the cradle 14. Connector 62 allows a second cable 66 to connect the cradle 14 (via connector 62) to an independent programming and data-logging computer 68, or the like and thereby connect through data/power connector 52 with the mobile detecting unit 12. Alternatively, the computer 68 may communicate directly with the mobile detecting unit 12 via cable 66 attaching to data connector 45.

Generally, a direct connection between the computer 68 and mobile detecting unit 12 will be used only during an initial calibration procedure when constant reference to the computer 68 will be required. For all other times, the mobile detecting unit 12 will communicate with the computer 68 (for example during periodic downloading of data) via the cradle 14 and the joining of data/power connectors 44 and 52. While mobile detecting unit 12 is in the cradle 14, the mobile detecting unit 12 may exchange data with the computer 68 and may receive power for operation and for charging internal batteries as will be described.

Figure 4:
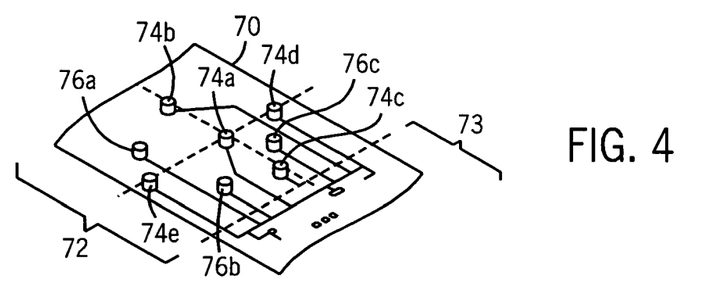
FIG. 4 is a fragmentary view of a printed circuit board positioned beneath the target markings of the units of FIGS. 1 and 2, the printed circuit board providing a number of detectors for measuring radiation flux and/or energy.

Referring now to FIGS. 1 and 4, positioned within the housing 20 parallel to, and centered between, photon-receiving face 16 and electron-receiving face 18 is a printed circuit board 70 having a detector zone 72 located beneath the targets 22 and 22'. Positioned on the printed circuit board 70 and centered in the detector zone 72 is a central detector 74a. Positioned on either side of detector 74a along a longitudinal axis of the printed circuit board 70 are detectors 74b and 74c whereas positioned on either side of detector 74a along a lateral axis of the printed circuit board 70 are detectors 74d and 74e. Detector 74b, 74c, 74d, and 74e are located at midpoints between detector 74a and the edge of the radiation field as defined by the targets 22 and 22'.

Detectors 74a–74e detect radiation flux and may be, for example, ionization detectors, solid-state detectors, or other detector types known in the art. Detector 74a provides a measurement of the central flux of the radiation beam and together with detectors 74b–74e provides indication of the variation in that flux over the area of the targets 22 and 22' as may form the basis of a measure of flatness and symmetry. Multiple measurements from detector 74a over time provides a measure of flux constancy.

Also positioned on the printed circuit board 70 in the detector zone 72 are energy-detectors 76a, 76b, and 76c. Energy detectors 76a, 76b, and 76c may be located arbitrarily within the detector zone 72 but are preferably equidistant from the detector 74a to reduce the effects of variations of the beam profile on the their signals. These detectors directly measure radiation flux but include filters and other elements which allow the energy of the radiation beam to be determined from the flux signals. Detectors 74 and 76 will be described in more detail below.

Figure 5:
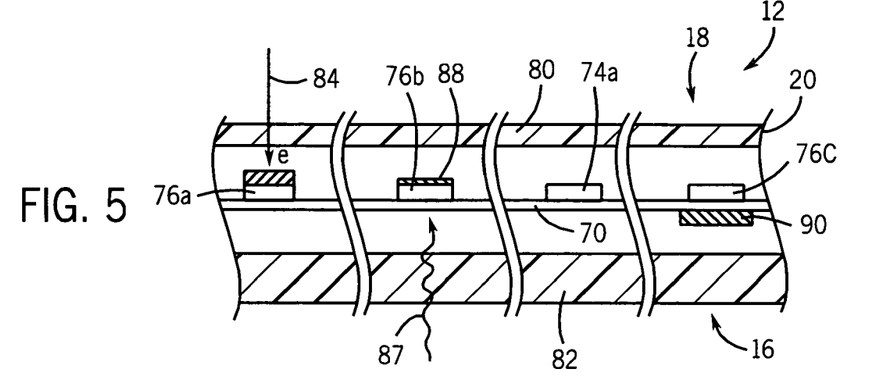
FIG. 5 is a cross-sectional view through several detectors of FIG. 4 and front and rear buildup materials of the housing showing passage of electron radiation and photon radiation through different build-up materials (for all detectors) and different filtration materials (for particular detectors) and a backscatter material (for one detector)

Referring to FIGS. 4 and 5, the printed circuit board 70 positions the detectors 74 and 76 between build-up material 80 on electron-receiving face 18 of the housing 20 and build-up material 82 on the photon-receiving face 16 of housing 20. During use, therefore, electrons 84 will arrive at detectors 74 and 76 after passing through build-up material 80 and photons 87 will arrive at detectors 74 and 76 after passing through build-up material 82. Each of build-up materials 80 and 82 is optimized for the particular type of radiation it is intended to receive. In the preferred embodiment, the build-up material 80 is a plastic material equivalent to 1.5 centimeters of water optimized for electrons and a build-up material 82 is a plastic material equivalent to 3.5 centimeters of water optimized for photons. More generally, the amount of build-up material 80 and 82 is selected to increase the sensitivity of the detectors 74 and 76 to the particular mode of radiation and to provide even sensitivity of the detectors 74 and 76 (ignoring for the moment any filtration) to the expected energy range of the particular radiation mode.

Referring specifically to FIG. 5, detectors 74a–74d are intended to measure radiation flux directly and have no additional filtration. Energy-detectors 76a, 76b, and 76c, however, have additional filter and backscatter elements to allow them to distinguish among different energies of radiation. In the preferred embodiment, detector 76a has 10 mm of aluminum 86 on its side toward electron-receiving face 18 and energy-detector 76b has 1 mm of aluminum 88 on its side toward electron-receiving face 18. Energy-detector 76c, in contrast, provides no filtration material on its die toward electron-receiving face 18, but on the side closest to photon-receiving face 16 provides 6 mm of lead. This lead provides backscatter of electrons coming through electron-receiving face 18, which hit the lead 90 and scatter back into energy-detector 76. The lead may alternatively be a brass disk.

The filtration and backscatter element cause each of these energy detectors 76a, 76b, and 76c to produce a slightly different signal. When combined, these signals provide a discrimination of different energies as will be described below.

Figure 6:
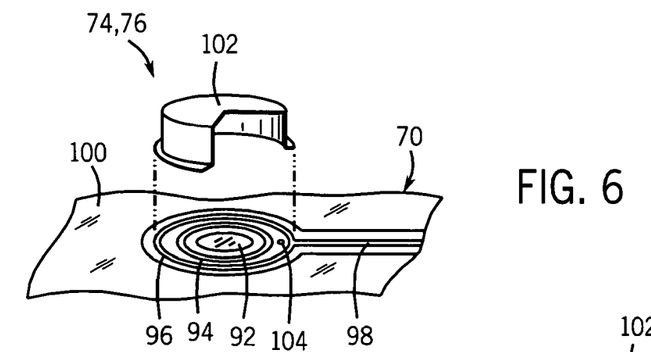
FIG. 6 is an exploded perspective view of one of the detectors of FIG. 4 showing its assembly from a cap placed on exposed traces of a printed circuit board.

Referring now to FIG. 6, in the preferred embodiment, each of detectors 74–76 is an ionization detector of a type in which ionized gas provides a path of conduction between charged and separated plates, and are manufactured using printed circuit board techniques such as those employing a photoresist/etching process or the like.

In particular, a manufacturing technique of the present invention provides circular disk-shaped collector 92 on the upper surface of the printed circuit board 70 to provide one charged plate. The collector is surrounded by a guard ring 94, which in turn is surrounded by a high voltage ring 96 leading by trace 98 to a high voltage source. The remainder of the surface of the printed circuit board 70, in near proximity to the detector 74 or 76, may include a ground plane 100.

A brass cap 102 being a hollow cylinder with an open lower base may be attached at the edge of the lower base to the high voltage ring 96 by solder, or the like. The upper solid base of the brass cap is preferably approximately 0.25 mm thick. A vent port 104 is drilled through the printed circuit board 70 to provide pressure equalization to the inner surface of the brass cap 102, which holds ionizing air at ambient pressure. Alternatively, the vent port 104 could be drilled through the brass cap 102. Other materials than brass can be used for the cap as will be understood to those of ordinary skill in the art. A chamber created within the cap and upper surface of the printed circuit board encloses approximately 0.6 cubic cm of air.

Figure 7:
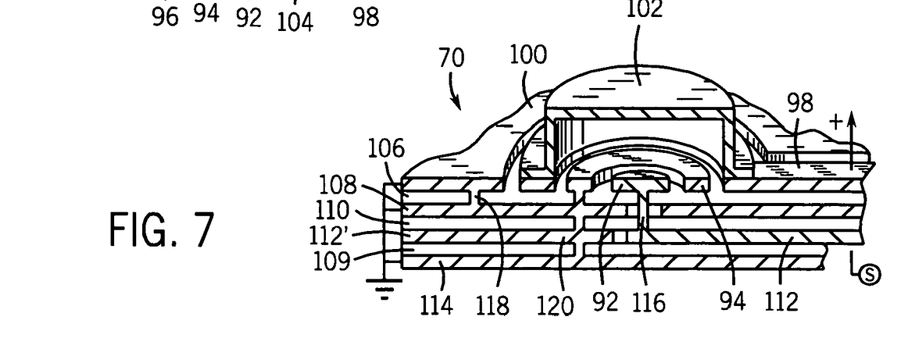
FIG. 7 is a perspective cross-sectional view of the assembled ionization detector FIG. 6 showing the multiple layers of the printed circuit board used to provide shielding of the detected signals.

Referring to FIG. 7, the printed circuit board 70 may be a multi-layer printed circuit board having the upper layer shown in FIG. 6 providing copper cladding forming the collector 92, guard ring 94, high voltage ring 96, and ground plane 100. Beneath and supporting this upper layer is an insulator 106 and then a ground plane 108. Beneath the ground plane 108 is another insulator 110, followed by a signal plane 112 another insulator 109 and finally an outer ground plane 114. The printed circuit board 70 may be standard copper clad epoxy-impregnated fiberglass.

Generally, the signal plane 112 includes multiple traces, one connecting to collector 92 by via 116. The ground plane 100 may be joined by vias 118 and 120 to guard ring 94 and ground planes 108 and 114, the former which may provides holes through which via 116 may pass. As apparent from FIG. 7, the traces of the signal plane 112 are thus always flanked on their upper, lower, right and left surfaces by ground planes 114 and 108 providing shielding to the signals detected signals.

Figure 8:
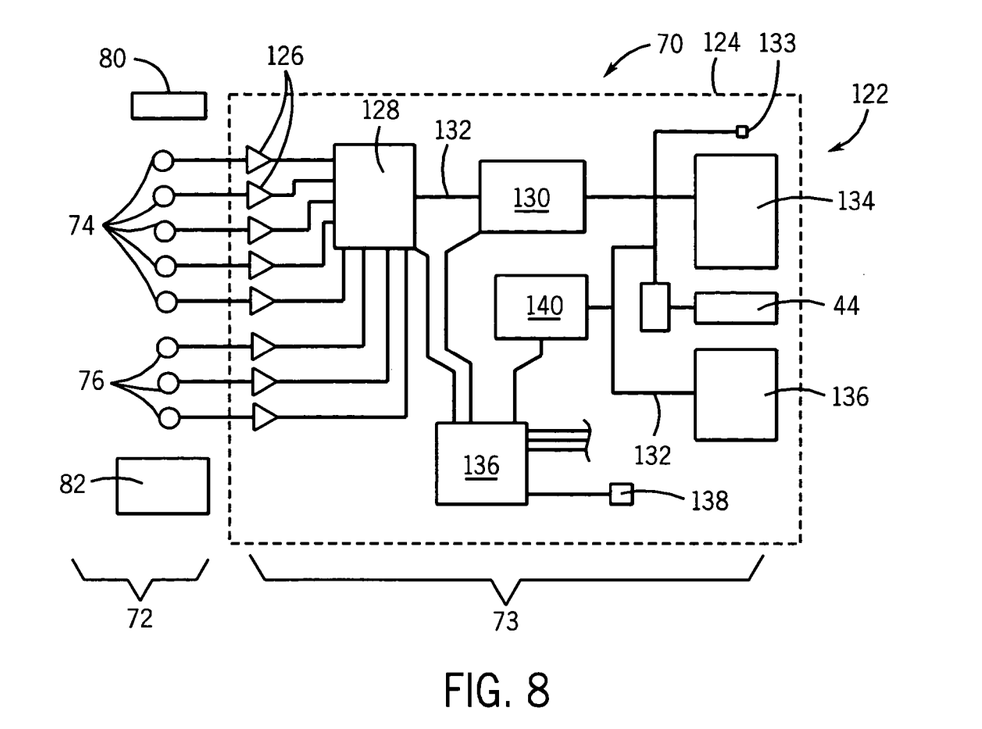
FIG. 8 is a block diagram of the circuitry of the detector of FIG. 1, such as may be placed on the circuit board of FIG. 4 and which employs a microprocessor based processing system to store data within an associated memory for later communication through a port.

Referring now to FIGS. 4 and 8, the traces of the signal plane 112 and the ground planes 108, 100, and 114 and high voltage traces 98 may pass out of the detector zone 72 to a circuit area 73 also on the circuit board 70 but displaced from the targets 22 and 22' and positioned between radiation shields 124. The circuit area 73 holds processing circuitry 122 including amplifiers 126 receiving signals from the signal plane 112. The amplifiers 126 connect to a multiplexing A to D converter 128 providing digitized signals to a processor 130 via an internal bus 132.

The processor 130 accesses an internal clock and calendar and communicates with a temperature and barometric pressure sensor 134 to correct for changes of ionization detectors caused by changes in ambient atmospheric pressure and temperature (as is understood in the art), with an audible annunciator 133, the RS-232 data/power connector 44, the controls 137 of the first side wall 24 including: the alphanumeric display 26, the reset button 28 the LED 29, the radiation mode captions lamps 30, and the mode select button 32. The processing circuitry 122 of the circuit area 73 may also include power supply 136 communicating via a jack 138 with the power cord 58 shown in FIG. 2.

The processor 130 executes a program stored in memory 140 to process the signals received from the detectors 74 and 76 and to store them in memory 140 as will be described. The program accepts inputs from the temperature and barometric pressure sensor 134, the RS-232 data/power connector 44, the reset button 28, and the mode select button 32 and provides outputs to the LED 29, RS-232 data/power connector 44, the alphanumeric display 26, and the radiation mode captions lamps 30 according to the inputs and the logic of the control program described herein.

Figure 11:
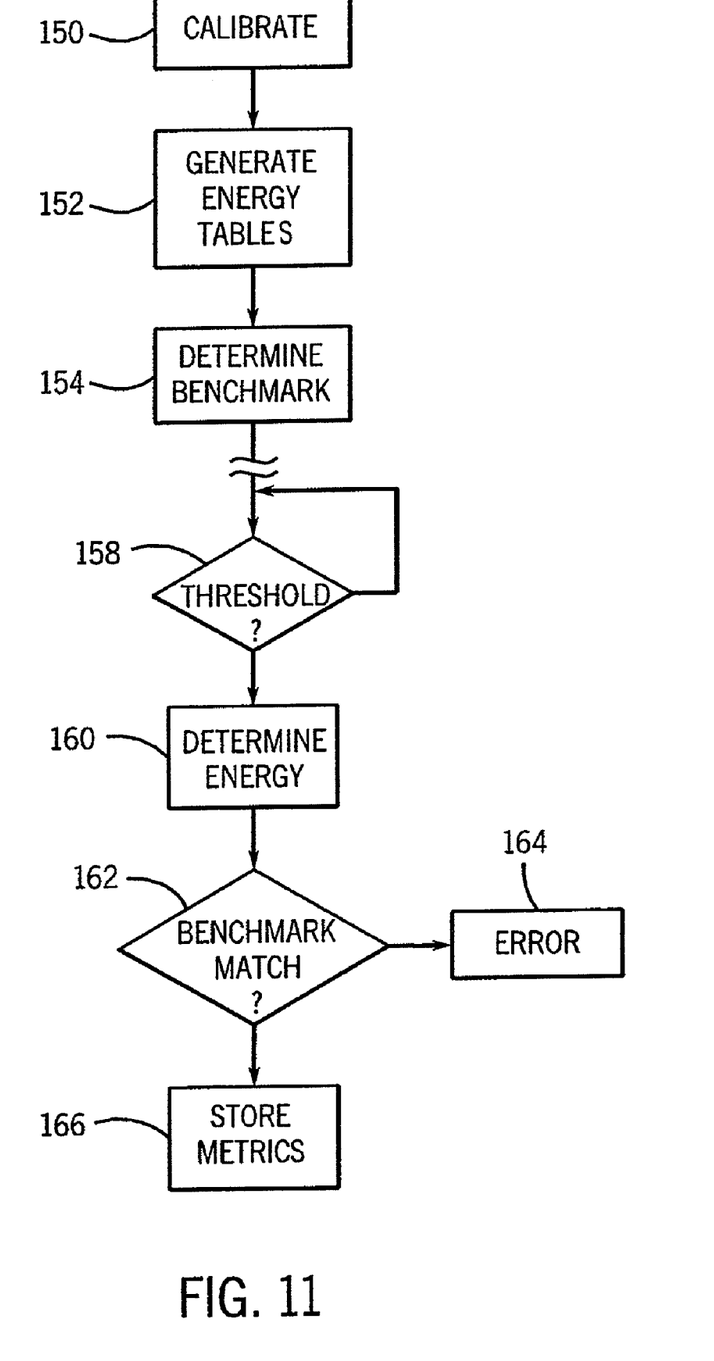
FIG. 11 is a flow chart of a program executed by the microprocessor of the circuit of FIG. 8 in implementing the present invention.

Referring now to FIGS. 2 and 11, the present invention is used in three distinct phases. In a first phase, the mobile detecting unit 12 is connected to computer 68 by cable 66 and instructed by software in the computer 68 to enter a calibrate mode as indicated by process block 150. During this calibrate mode, the mobile detecting unit 12 is exposed to radiation from a radiotherapy machine (not shown) at each energy level and for each radiation mode. The energy of radiation is identified via the operator of the computer 68 and the mode identified by the mode select button 32 and matched to an energy signature determined from the measurements of the energy detectors 76a–76c.

Figure 9:
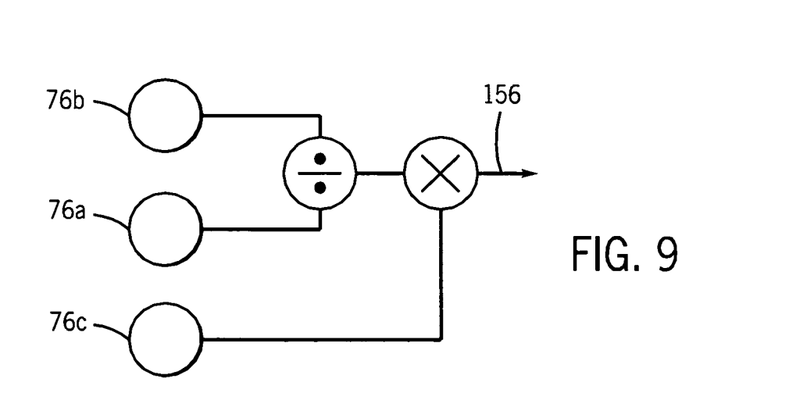
FIG. 9 is a flow diagram showing the calculation of energy for electron radiation.

Referring momentarily to FIG. 9, for electrons, the energy signature value is determined by taking the signal from detector 76b having 1 mm of aluminum and dividing it by the signal from detector 76a having 10 mm of aluminum. This fraction is multiplied by the backscatter signal from detector 76c having a backstop of 6 mm of lead to produce the electron energy signature value 156.

Figure 10:
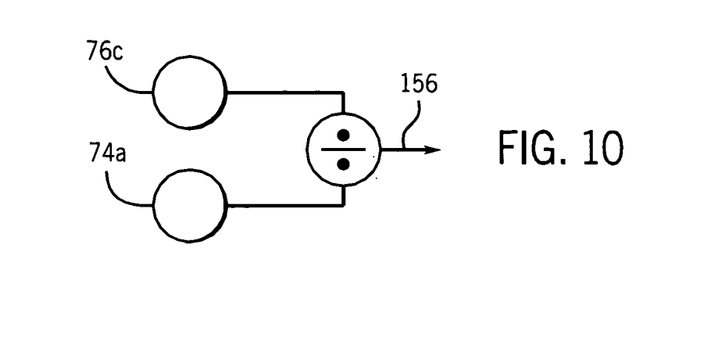
FIG. 10 is a figure similar to that of FIG. 9 showing the calculation of energy for photon radiation.

For photons as shown in FIG. 10, the signal from detector 76c having the 6 mm of lead as a backstop is divided by a signal from the center detector 74 to produce a photon energy signature value 156.

It will be understood that other algebraic combinations of these multiple detectors can be used and that generally the energy may be fit to a polynomial function of the signals from detectors 76 and/or 74.

The computer 68 then compiles, per process block 152, an energy table consisting of an entry for each energy and mode providing benchmark flux measurements from each of the detectors 74a–74d and the energy signature value 156. The energy table is downloaded into memory 140.

Referring again to FIG. 11, in a second phase of operation, the mobile detecting unit 12 is armed automatically and the LED 29 turns green and the indicators display "RDY" for ready. Then unit 12 is placed on the radiotherapy machine in the path of the radiation with the light field of the radiotherapy machine aligned with targets 22 or 22'. The operator selects the desired radiation mode corresponding with the orientation of the mobile detecting unit 12 and begins the radiation exposure. Once armed, the processor 130 monitors the signals from the detectors 74 and 76 per decision block 158 until the signals exceed a predetermined threshold indicating radiation is present.

Once this threshold is passed, at succeeding process block 160, the energy of the radiation is determined by matching the readings from detectors 74a and 76a–76c (as appropriate) to the energy signature value 156 stored in the energy table in memory 140 plus and minus a predetermined range. If the energy readings do not match with any energy signature value 156 stored in the energy table, the alphanumeric display 26 shows an error message ("ERR") and the LED 29 flashes red and there is an audible beep produced by an annunciator 133. No further readings can be taken until the reset button 28 is pressed whereupon the LED 29 returns to its default color of green.

Once the energy level of radiation has been determined, the processor 130 compares the benchmark flux measurements associated with the particular entry of the energy table, per decision block 162, to the signals from the detectors 74a–74d. The flatness and the symmetry of the current flux of the radiation beam is compared to a predetermined threshold value based on the benchmark flux measurements and the constancy of the flux is compared to a predetermined acceptable range also based on the benchmark flux values. Flatness is generally determined by finding the maximum and minimum values of the detectors 74a–74e (values of detectors indicated in the following by the detector number). Then, flatness=(Max(detectors 74a–74e)−Min(detectors 74a–74e)/(Max(detectors 74a–74e)+Min(detectors 74a–74e)). Symmetry is determined by axial=(top (detector 74b)−bottom (detector 74c))/bottom (detector 74c) and transverse=(right (detector 74d)−left (detector 74e))/left (74e). Constancy is determined by the center detector value over time: (detector 74a(at time x)−detector 74a (at benchmark time))/detector 74a (at benchmark time).

If the current flatness, symmetry of constancy is outside of a predetermined range related to the benchmark value, an error signal is indicated per process block 164 and the alphanumeric display 26 shows an error message ("ERR") alternating with the type of error ("SYM", "FLT", and "CST" for symmetry, flatness and constancy, respectively) and the LED 29 shows red and flashes together with an audible beep by the annunciator. No further readings can be taken until the reset button 26 is pressed whereupon LED 29 returns to its default color of green.

If the flux measurements are within the acceptable predetermined range, the alphanumeric display 26 shows and indicates the deduced energy level, and the unit resets itself. At process block 166, the flux values are stored in memory together with a date stamp maintained by the processor 130 as linked to the determined energy level.

The operator may then proceed through energy ranges and modes stopping only as necessary to flip the mobile detecting unit 12 according to the mode. When the measurements have been made, the operator may install the detecting unit 12 back on the cradle 14 and download the data to the computer 68 for additional analysis or preparation of automatic reports. The memory 140 is sized to hold up to thirty days worth of data so that downloading may be postponed as desired on any given day.

The third phase of operation is a wired version of phase two for real-time data collection. In this phase, the same functionality exists as is phase two, but beam checker 10 is hardwired either through the cradle 14 or directly to a remote computer 68 allowing real-time data collection and beam checker controls.

It is specifically intended that the present invention not be limited to the embodiments and illustrations contained herein, but include modified forms of those embodiments including portions of the embodiments and combinations of elements of different embodiments as come within the scope of the following claims.

We claim:

1. A test instrument for therapeutic radiation comprising:
   a set of spaced radiation flux-detectors providing flux signals;
   at least one radiation energy-detector providing an energy signal;
   a storage system for storing benchmark flux values associated with different energy ranges of a set of energy ranges; and
   processing circuitry comparing at least one of the flux signals to benchmark flux values automatically selected based on the energy range indicated by the energy signal to provide an indication of any improper operation of a measured radiation source.

2. The test instrument of claim 1 wherein the energy ranges are centered at energies selected from the group consisting of: 6, 9, 12, 16, and 22 MeV and 6, 18, and 23 MV.

3. The test instrument of claim 1 further including a display displaying one of the energy ranges.

4. The test instrument of claim 1 wherein the processing circuitry provides an alarm signaling an energy deviating more than a predetermined amount from a stored energy range.

5. The test instrument of claim 1 wherein the flux signals and benchmark flux values provide a measure of radiation flatness and wherein the processing circuitry provides an alarm when the radiation flatness indicated by the flux signals is more than a predetermined amount different from the radiation flatness indicated by the benchmark flux values for the corresponding energy range.

6. The test instrument of claim 1 wherein the flux signals and benchmark flux values provide a measure of radiation symmetry and wherein the processing circuitry provides an alarm when the radiation symmetry indicated by the flux signals is more than a predetermined amount different from the radiation symmetry indicated by the benchmark flux values for the corresponding energy range.

7. The test instrument of claim 1 wherein the processing circuitry provides an alarm when the flux signals are more than a predetermined amount different from benchmark flux values for the corresponding energy range.

8. The test instrument of claim 1 wherein the radiation energy-detector is a set of detectors having different filtration to provide radiation signals and wherein the energy signal is derived from an algebraic combination of the radiation signals from the set of detectors.

9. The test instrument of claim 1 wherein the radiation energy-detector is a set of detector elements providing radiation signals at least one of which detector element has a scatter element positioned behind it with respect to the measured radiation so that the detector element is sensitive to backscatter and wherein the energy signal is derived from an algebraic combination of the radiation signals.

10. A test instrument for therapeutic radiation comprising:
   a set of spaced radiation flux-detectors providing flux signals;
   at least one radiation energy-detector providing an energy signal;
   a storage system for storing benchmark flux values associated with a set of energy ranges; and
   processing circuitry comparing at least one of the flux signals to the benchmark flux values to provide an indication of any improper operation of a measured radiation source, further including:
   a housing providing opposed first and second faces and holding the radiation flux-detectors between the first and second faces;
   a first calibrating material for electrons positioned to intercept electrons passing through the first face to the radiation flux-detectors; and
   a second calibrating material for photons positioned to intercept photons passing through the second face to the radiation flux-detectors;
   whereby electrons may be measured with the housing in a first orientation by exposing the radiation flux-detectors through the first face and photons may be measured by flipping the housing to a second orientation and exposing the detectors through the second face.

11. The test apparatus of claim 10 wherein the first and second calibrating materials are build-up materials to optimize the sensitivity of the flux measurements for electrons and photons, respectively.

12. The test instrument of claim 10 wherein the first and second calibration materials are different thicknesses of a water equivalent material.

13. The test instrument of claim 10 wherein the apparatus includes an input for providing an indication of whether electrons or photons are being measured.

14. The test instrument of claim 13 wherein the input is a manually operated switch.

15. The test instrument of claim 10 further including a display indicating radiation type.

16. The test instrument of claim 10 further including a display indicating a quantitative radiation measurement.

17. The test instrument of claim 16 display is on a third face of the housing visible when either the first or second faces is lying against a surface.

18. The test instrument of claim 17 wherein the display flips its orientation according to whether electrons or photons are being measured so as to be upright to a operator when the housing is resting with the first or second face on a horizontal support.

* * * * *